United States Patent [19]

Michaely

[11] Patent Number: 4,692,185
[45] Date of Patent: Sep. 8, 1987

[54] N-(ORTHO-SUBSTITUTED) BENZYL, 3-TRIFLUOROMETHYLPHENOXY NICOTINAMIDES AS HERBICIDES

[75] Inventor: William J. Michaely, Richmond, Calif.

[73] Assignee: Stauffer Chemical Company, Westport, Conn.

[21] Appl. No.: 818,149

[22] Filed: Jan. 13, 1986

[51] Int. Cl.$^4$ .................. A01N 43/40; C07D 211/72
[52] U.S. Cl. ........................................ 71/94; 546/291
[58] Field of Search .................... 546/292, 291; 71/94

[56] References Cited

U.S. PATENT DOCUMENTS 4,270,946 6/1981 Gutman .............................. 546/292

FOREIGN PATENT DOCUMENTS 2140772 1/1973 France ................................ 546/292
2087887 6/1982 United Kingdom ................ 546/292

Primary Examiner—Henry R. Jiles
Assistant Examiner—Robert C. Whittenbaugh
Attorney, Agent, or Firm—Joel G. Ackerman

[57] ABSTRACT

Compounds having the formula

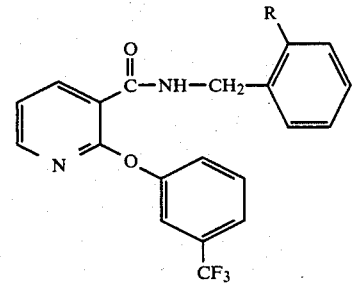

in which R is $C_1$–$C_4$ alkyl, $C_1$–$C_4$ haloalkyl or halogen, are herbicides.

11 Claims, No Drawings

N-(ORTHO-SUBSTITUTED) BENZYL, 3-TRIFLUOROMETHYLPHENOXY NICOTINAMIDES AS HERBICIDES

This invention relates to novel herbicidal compounds having the formula

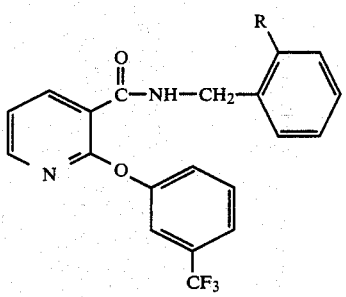

in which R is $C_1$–$C_4$ alkyl, $C_1$–$C_4$ haloalkyl or halogen.

The alkyl and alkoxy groups may be straight or branched chain having 1 to 4 carbon atoms apiece, such as methyl, ethyl, methoxy, ethoxy, and the various propyl, butyl, propoxy and butoxy groups. Of these, methyl and methoxy are preferred.

The haloalkyl moieties may be similarly be any of the alkyl moieties having from 1 to 4 carbon atoms, substituted by one or more halogens. Preferably, the alkyl group is a methyl substituted by from 1 to 3 halogens. Most preferred of this class is trifluoromethyl. The term "halogen", whenever used herein, includes fluorine, chlorine, bromine and iodine.

The compounds of this invention have been found to be active herbicides in possessing both pre- and post-emergence herbicidal activity against various species of weeds, and have demonstrated selective control of weeds in certain crops, notably cereals.

This invention also therefore relates to a method for controlling undesirable vegetation, particularly undesirable grassy vegetation, comprising applying to a locus where control of such vegetation is desired, preferably prior to the emergence of such undesirable vegetation, a herbicidally effective amount of a compound as described herein, and also relates to herbicidal compositions of matter comprising a herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

In general, the compounds of the present invention can be prepared by reaction of the appropriate 2-(3-trifluoromethylphenoxy)nicotinoyl chloride with the appropriate benzyl amine.

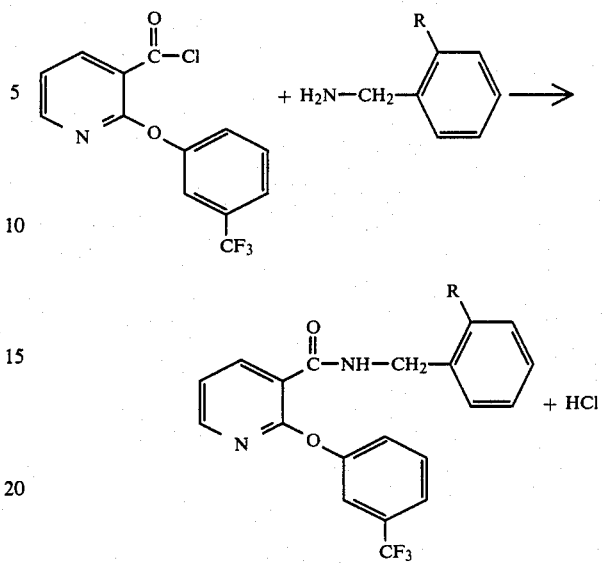

in which R is as previously defined. This reaction is carried out in the presence of an acid acceptor such as caustic, an additional equivalent of the reacting amine, or another amine (for instance triethylamine). Reaction temperatures may range from about 0° to about 110° at atmospheric pressure. Any of a number of solvents may be used, such as methylene chloride, diethyl ether, benzene and toluene, the first mentioned being preferred.

The starting material nicotinoyl chlorides are prepared from the corresponding carboxylic acids by any conventional techniques, such as reacting the acid with a suitable chlorinating agent, for instance phosgene, thionyl chloride, oxalyl chloride, or phosphorus tri- or pentachloride. The phenoxy nicotinic acids may be prepared by reacting meta-trifluoromethylphenol with 2-chloronicotinic acid, as described by Villani, et al., *J. Medicinal Chemistry*, Vol. 18, p. 1 (1975).

The following represents an example of the preparation of a compound according to the present invention.

EXAMPLE 1

Preparation of 2-(3-Trifluoromethylphenoxy-N-(2′-fluorobenzyl)-nicotinamide (Compound 3 herein)

In a flask were placed 4 grams (g) (0.01326 mole) 2-(3-trifluoromethylphenoxy)nicotinoyl chloride, dissolved in methylene chloride. There was then added 1.7 g (0.01326 mole) of 2-fluorobenzylamine, very slowly, with vigorous stirring. After about 15 minutes, 1.34 g (0.01326 mole) of triethylamine was added dropwise. The reaction mixture was stirred for a short time, then heated intensely for about 5 minutes and allowed to return to room temperature. After approximately ½ hour, 5% aqueous sodium carbonate solution was added with stirring continued. The aqueous and organic phases were separated; the aqueous phase was decanted off and the organic phase washed twice with 5% sodium carbonate solution and twice with water. The organic phase was then dried over sodium sulfate; solvent was stripped off, and an oil-like mixture was recovered, which crystallized in a short time. The solid was then washed with pentane to remove any remaining amine. There was obtained 3.5 g (67% of theoretical yield) which was identified as the desired compounds by infrared, nuclear magnetic resonance, and mass spectroscopic analysis.

Representative compounds according to this invention are depicted in the following Table I.

TABLE I

[Structure: pyridine ring with C(=O)-NH-CH2-phenyl(R) substituent at position 3 and O-phenyl(CF3) substituent at position 2]

| Compound No. | R | m.p., °C. |
|---|---|---|
| 1 | Cl | 93–95 |
| 2 | CH₃ | 100–104 |
| 3 | F | 90–93 |
| 4 | Br | 107–110 |
| 5 | CF₃ | 104–107 |

The compounds listed in the foregoing Table I were tested for herbicidal activity as follows:

Pre-Emergence Herbicide Screening Test

Flats were filled with sandy loam soil containing a fungicide and fertilizer. The soil was leveled and rows of three grassy weeds, four broadleaf weeds and yellow nutsedge (*Cyperus esculentus*), were planted thickly enough so that several seedlings emerged per inch of row. The grassy weeds were: foxtail (Setaria spp.), watergrass (*Echinochloa crusgalli*) and wild oat (*Avena fatua*). Broadleaf weeds utilized were annual morningglory (*Ipomoea purpurea*), velvetleaf (*Alutilon theophrasti*), mustard (*Brassica juncea*), and curly dock (*Rumex crispus*).

The flats wer placed in a greenhouse at 70°–85° F., and watered by sprinkling. One day after planting the flats were sprayed with a solution of a test compound at a rate of 80 gallons of solution per acre with the compound being applied at a rate of 4 pounds per acre (4.48 kg/ha).

The solutions of the test compounds were made by weighing out 300 mg of the compound in question into a 120 ml wide-mouth bottle, dissolving it in 50 ml of acetone containing 1% polyoxyethylene sorbitan monolaurate emulsifier and then diluting to 100 ml with water. Additional solvents, not exceeding 5 ml, were used if needed to dissolve the compound.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°–85° F. and watered by sprinkling. Nine to eleven days after planting, the flats were sprayed on a table at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage for three days. Thereafter, they were watered daily by sprinkling. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE II

| | Pre-emergence Control (4.48 kg/ha) | | | Post-Emergence control | | |
|---|---|---|---|---|---|---|
| Compound Number | grasses | broadleaf weeds | nutsedge | grasses | broadleaf weeds | nutsedge |
| 1 | 97 | 94 | 0 | 73 | 76 | 0 |
| 2 | 93 | 84 | 0 | 68 | 85 | 0 |
| 3 | 100 | 100 | 0 | 87 | 90 | 10 |
| 4 | 87 | 78 | 0 | 67 | 74 | 5 |
| 5 | 93 | 54 | 0 | 40 | 61 | 0 |

Pre- and Post-Emergence multi-weed/multi-crop evaluation

Compounds were evaluated at various application rates ranging from 2.0 to 0.125 pound active ingredient/acre (2.24 and 0.128 kg/ha, respectively) for pre- and post-emergence activity against a number of weed and crop species. The procedures were generally similar to those described above. Broadleaf weed species utilized were annual morningglory, nightshade, velvetleaf, mustard, cocklebur (*Xanthium pennsylvanicum*), sesbania (*Sesbania* spp.), and two of the following: sicklepod (*Cassia obtusifolia*), pigweed (*Amaranthus retroflexus*), broadleaf signalgrass (*Brachiaria platyphylla*) and spurred anoda (Anoda spp.). Grassy weeds utilized were: foxtail, watergrass, wild oat, downy brome (*Bromus tectorum*), annual ryegrass (*Lolium multiflorum*) and shattercane (*Sorghum bicolor*). Yellow nutsedge was also included in these tests. Crops included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*).

The following Tables III and IV contain the results of these tests, in terms of average control of the seven broadleaf weeds, six grassy weeds, and nutsedge, and injury to the crop species, with visual ratings ranging from 0% (no injury) to 100% (complete kill) as compared to untreated control flats.

TABLE III

(Pre-Emergence Control)

| Cmpd. No. | Rate lb/A | grassy weeds | broadleaf weeds | nut-sedge | soy-bean | wheat | milo | rice | sugar-beets | corn | cotton |
|---|---|---|---|---|---|---|---|---|---|---|---|
| 1 | 2.0 | 75 | 71 | 0 | 35 | 0 | 20 | 15 | 100 | 15 | 10 |
|   | 0.5 | 62 | 56 | 0 | 20 | 0 | 15 | 10 | 60 | 10 | 10 |
|   | 0.25 | 51 | 23 | 0 | 0 | 0 | 10 | 10 | 60 | 5 | 10 |
| 2 | 2.0 | 90 | 75 | 25 | 35 | 10 | 70 | 20 | 100 | 45 | 40 |
|   | 1.0 | 87 | 63 | 25 | 25 | 10 | 45 | 0 | 90 | 35 | 25 |
|   | 0.5 | 76 | 50 | 0 | 20 | 0 | 25 | 0 | 85 | 15 | 15 |
|   | 0.25 | 20 | 37 | 0 | 10 | 0 | 10 | 0 | 70 | 0 | 15 |
| 3 | 2.0 | 72 | 81 | 0 | 35 | 0 | 90 | 50 | 100 | 55 | 10 |
|   | 1.0 | 61 | 58 | 0 | 10 | 0 | 90 | 20 | 100 | 30 | 10 |
|   | 0.5 | 48 | 31 | 0 | 0 | 0 | 75 | 0 | 90 | 25 | 0 |
|   | 0.25 | 19 | 26 | 0 | 0 | 0 | 40 | 0 | 90 | 0 | 0 |
| 4 | 2.0 | 86 | 60 | 0 | 15 | 0 | 35 | 0 | 99 | 15 | 40 |
|   | 1.0 | 63 | 37 | 0 | 0 | 0 | 15 | 0 | 50 | 0 | 15 |
| 5 | 2.0 | 80 | 96 | 0 | 60 | 20 | 45 | 0 | 100 | 40 | 45 |
|   | 0.5 | 74 | 92 | 0 | 60 | 15 | 35 | 0 | 100 | 15 | 20 |

TABLE IV

(Post-Emergence Control)

| Cmpd. No. | lb/A | grassy weeds | broadleaf weeds | nut-sedge | soy-bean | wheat | milo | rice | beets | corn | cotton |
|---|---|---|---|---|---|---|---|---|---|---|---|
| 1 | 2.0 | 13 | 61 | 0 | 45 | 15 | 25 | 0 | 35 | 35 | 45 |
|   | 0.5 | 8 | 61 | 0 | 45 | 0 | 20 | 0 | 35 | 35 | 45 |
|   | 0.25 | 6 | 57 | 0 | 45 | 0 | 20 | 0 | 35 | 30 | 35 |
|   | 0.125 | 2 | 53 | 0 | 45 | 0 | 15 | 0 | 35 | 25 | 35 |
| 2 | 2.0 | 66 | 76 | 15 | 80 | 0 | 60 | 0 | 65 | 55 | 80 |
|   | 1.0 | 63 | 75 | 10 | 75 | 0 | 45 | 0 | 60 | 50 | 80 |
|   | 0.5 | 34 | 71 | 0 | 75 | 0 | 20 | 0 | 40 | 15 | 80 |
|   | 0.25 | 22 | 60 | 0 | 70 | 0 | 10 | 0 | 40 | 10 | 80 |
| 3 | 2.0 | 50 | 82 | 0 | 100 | 30 | 30 | 10 | 75 | 30 | 65 |
|   | 1.0 | 36 | 74 | 0 | 75 | 0 | 15 | 10 | 55 | 30 | 65 |
|   | 0.5 | 28 | 63 | 0 | 75 | 0 | 0 | 10 | 35 | 25 | 65 |
|   | 0.25 | 19 | 49 | 0 | 40 | 0 | 0 | 10 | 30 | 20 | 55 |

Post-Emergence Evaluation in Paddy Rice

Test compounds were evaluated for post-emergence control of weeds in paddy rice, with compounds variously applied pre-flood and post-flood. The tests were conducted as follows.

Tubs were filled to a depth of 2 inches with loamy sand soil pretreated with the previously used fungicide and 18-18-18 fertilizer. One pint of soil was removed; the resulting soil was leveled and five rows impressed. There were planted tubers of yellow nutsedge (YN) and seeds of watergrass (WG), annual morningglory (AMG), sesbania (SES) and M-9 variety of rice (*Oryzae sativa*). The pint of soil was then used to cover the seeds and tubers to a depth of 0.5 inches. The tubs were placed in a greenhouse and irrigated by sprinkling as necessary to keep the soil moist.

Two types of post-emergence evaluations were conducted. In one type, compounds were applied to the soil by spraying at indicated rates ranging from 2 lb/A to 0.25 lb/A (2.24 kg/ha to 0.28 kg/ha). Several days after application, the soil was covered with two inches of water. The type of test is referred to in the following Table V as the "PRE" test, namely pre-flood application.

In the second test, the soil was covered with two inches of water 7 to 10 days after the original seeding. Test compounds were then applied by pipetting into the water a stock solution of the compound dissolved in acetone at various levels ranging from 4 lb/A to 0.25 lb/A (4.48 kg/ha to 0.28 kg/h). This test is referred to in Table V as the "PO" or post-flood application of test compounds.

Three weeks after application the plant species were rated visually in terms of percent control from 0 to 100%, with 0% representing no injury and 100% representing complete kill, as compared to an untreated check plot. The results are shown in the following Table V.

TABLE V

(Post-Emergence Paddy Rice)

| Cmpd. No. | Application Method | Application Rate, (lb/A) | YNS | WG | AMG | SES | RICE |
|---|---|---|---|---|---|---|---|
| 1 | PO | 4.0 | 20 | 100 | 20 | 100 | 10 |
|   |    | 2.0 | 0 | 90 | 20 | 70 | 5 |
| 2 | PRE | 2.0 | 30 | 100 | 100 | 100 | 30 |
|   |     | 1.0 | 30 | 92 | 92 | 100 | 25 |
|   |     | 0.5 | 10 | 70 | 90 | 100 | 10 |
|   |     | 0.25 | 0 | 30 | 95 | 95 | 0 |
|   | PO | 4.0 | 40 | 100 | 50 | 90 | 40 |
|   |    | 2.0 | 30 | 100 | 45 | 95 | 35 |
|   |    | 1.0 | 30 | 95 | 40 | 95 | 15 |
|   |    | 0.5 | 10 | 20 | 20 | 75 | 10 |
|   |    | 0.25 | 0 | 10 | 20 | 100 | 0 |
| 3 | PRE | 2.0 | 60 | 100 | 95 | 100 | 50 |
|   |     | 1.0 | 25 | 92 | 80 | 97 | 15 |
|   |     | 0.5 | 10 | 90 | 90 | 90 | 0 |
|   |     | 0.25 | 0 | 30 | 30 | 60 | 0 |
|   | PO | 2.0 | 60 | 100 | 95 | 95 | 30 |
|   |    | 1.0 | 40 | 100 | 82 | 70 | 25 |
|   |    | 0.5 | 30 | 80 | 70 | 20 | 0 |
|   |    | 0.25 | 10 | 40 | 0 | 15 | 0 |
| 4 | PRE | 2.0 | 0 | 20 | 100 | 100 | 0 |
|   |     | 1.0 | 0 | 15 | 95 | 95 | 0 |
|   | PO | 4.0 | 0 | 95 | 10 | 90 | 0 |
|   |    | 2.0 | 0 | 77 | 35 | 47 | 0 |
|   |    | 1.0 | 0 | 40 | 20 | 70 | 0 |
| 5 | PRE | 2.0 | 0 | 95 | 70 | 95 | 30 |
|   |     | 1.0 | 0 | 90 | 70 | 95 | 30 |

TABLE V-continued

| | | (Post-Emergence Paddy Rice) | | | | | |
|---|---|---|---|---|---|---|---|
| Cmpd. No. | Application Method | Application Rate, (lb/A) | % Control | | | | |
| | | | YNS | WG | AMG | SES | RICE |
| | PO | 4.0 | 0 | 95 | 10 | 80 | 50 |
| | | 2.0 | 0 | 87 | 15 | 42 | 40 |
| | | 1.0 | 0 | 85 | 20 | 10 | 20 |

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | |
|---|---|
| Ingredient | Weight % |
| Oil | |
| Active Compound | 1 |
| Oil solvent-heavy aromatic naphtha | 99 |
| Total | 100 |
| Emulsifiable Concentrate | |
| Active Compound | 50 |
| Kerosene | 45 |
| Emulsifying agent (mixture of long chain ethoxylated polyethers with long chain sulfonate) | 5 |
| Total | 100 |
| Emulsifiable Concentrate | |
| Active Compound | 90 |

-continued

| EXAMPLES OF TYPICAL COMPOSITIONS | |
|---|---|
| Kerosene | 5 |
| Emulsifying agent (mixture of long chain ethoxylated polyethers with long chain sulfonate) | 5 |
| Total | 100 |

Dusts and/or Powders

| Ingredient | Wt. % | Wt. % | Wt. % |
|---|---|---|---|
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A compound having the formula

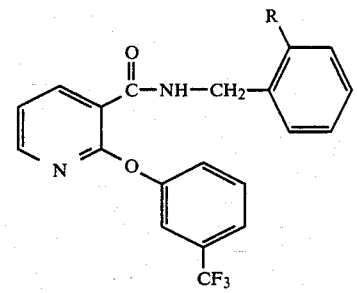

in which R is methyl, trifluoromethyl or bromo.

2. A compound according to claim 1 in which R is bromo.

3. A compound according to claim 1 in which R is methyl.

4. A compound according to claim 1 in which R is trifluoromethyl.

5. A method of controlling undesirable vegetation comprising applying to said vegetation or to a locus where control is desired a herbicidally effective amount of a compound according to claim 1.

6. A method according to claim 5 in which the compound is applied prior to the emergence to the undesirable vegetation.

7. A method according to claim 5 in which the compound is applied subsequent to the emergence to the undesirable vegetation.

8. A method according to claim 5 comprising controlling undesirable vegetation in the presene of a cereal crop.

9. A method according to claim 8 in which the crop is rice.

10. A method according to claim 8 in which the crop is wheat.

11. A herbicidal composition comprising: (a) a herbicidally effective amount of a compound according to claim 1 and (b) a herbicidally suitable inert diluent or carrier.

* * * * *